United States Patent
Zarrouk et al.

(10) Patent No.: US 9,956,041 B2
(45) Date of Patent: May 1, 2018

(54) ROBOT FOR MINIMALLY INVASIVE NEUROSURGERY

(71) Applicant: TECHNION RESEARCH & DEVELOPMENT FOUNDATION LTD., Haifa (IL)

(72) Inventors: David Zarrouk, Jerusalem (IL); Moshe Shoham, Hoshaya (IL); Menashe Zaaroor, Tiberias (IL); Hadas Ziso, Kiryat Tivon (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 976 days.

(21) Appl. No.: 13/941,607

(22) Filed: Jul. 15, 2013

(65) Prior Publication Data
US 2014/0025088 A1    Jan. 23, 2014

Related U.S. Application Data

(63) Continuation of application No. PCT/IL2012/000022, filed on Jan. 15, 2012.
(Continued)

(51) Int. Cl.
*A61B 19/00*    (2006.01)
*A61B 34/30*    (2016.01)
(Continued)

(52) U.S. Cl.
CPC .......... *A61B 19/2203* (2013.01); *A61B 34/30* (2016.02); *A61B 90/11* (2016.02);
(Continued)

(58) Field of Classification Search
CPC ..... A61B 10/0233; A61B 34/30; A61B 90/11; A61B 2034/301–2034/304
(Continued)

(56) References Cited

U.S. PATENT DOCUMENTS 6,491,699 B1 * 12/2002 Henderson ............ A61B 19/52
600/414
6,527,782 B2 * 3/2003 Hogg ................ A61B 17/3417
128/899
(Continued)

OTHER PUBLICATIONS

R.E Skelton et al., "Chapter 17: An Introduction to the Mechanics of Tensegrity Structures," in The Mechanical Systems Design Handbook: Modeling, Measurement, and Control, 2001, CRC Press.
(Continued)

*Primary Examiner* — Diane Yabut
*Assistant Examiner* — Erich Herbermann
(74) *Attorney, Agent, or Firm* — Daniel J. Swirsky; AlphaPatent Associates Ltd.

(57) ABSTRACT

A robotic device for performing intracranial procedures, comprising a baseplate for mounting on the subject's skull and a rotatable base element rotating on the baseplate. The rotatable base element has a central opening through which a cannulated needle can protrude such that it can rotate around an axis perpendicular to the baseplate. This cannulated needle is robotically controlled to provide motion into and out of the subject's skull. A flexible needle is disposed coaxially within the cannulated needle, and it is controlled to move into and out of a non-axial aperture in the distal part of the cannulated needle. Coordinated control of the insertion motion of the cannulated and flexible needles, and rotation of the combined cannulated/flexible needle assembly enables access to be obtained to a volume of a region of the brain having lateral dimensions substantially larger than the width of the cannulated needle.

19 Claims, 9 Drawing Sheets

Related U.S. Application Data

(60) Provisional application No. 61/457,147, filed on Jan. 14, 2011.

(51) Int. Cl.
*A61B 90/11* (2016.01)
*A61B 10/02* (2006.01)
*A61B 34/20* (2016.01)
*A61B 90/00* (2016.01)

(52) U.S. Cl.
CPC .......... *A61B 10/0233* (2013.01); *A61B 90/39* (2016.02); *A61B 2034/2059* (2016.02)

(58) Field of Classification Search
USPC ........................................ 606/130
See application file for complete search history.

(56) References Cited

U.S. PATENT DOCUMENTS

| | | |
|---|---|---|
| 2004/0059260 A1 | 3/2004 | Truwit |
| 2004/0144395 A1* | 7/2004 | Evans ............ A61B 17/06066 128/885 |
| 2006/0190055 A1* | 8/2006 | Malinowski ........ A61N 1/0529 607/45 |
| 2008/0171990 A1 | 7/2008 | Zauner |
| 2009/0048610 A1* | 2/2009 | Tolkowsky ............ A61B 90/11 606/130 |
| 2009/0048622 A1 | 2/2009 | Wilson |
| 2009/0171184 A1 | 7/2009 | Jenkins et al. |
| 2010/0160733 A1* | 6/2010 | Gilboa ............... A61B 1/00154 600/117 |
| 2010/0241155 A1* | 9/2010 | Chang ............... A61B 17/3421 606/196 |

OTHER PUBLICATIONS

International Search Report and Written Opinion in PCT Application No. PCT/IL2012/000022 dated May 25, 2012.

\* cited by examiner

ROBOT FOR MINIMALLY INVASIVE NEUROSURGERY

CROSS-REFERENCE TO RELATED APPLICATIONS

This application is a continuation-in part of PCT International Application No. PCT/IL2012/000022, which has an international filing date of Jan. 15, 2012, and which claims the benefit of priority from U.S. Provisional Patent Application No. 61/457,147, filed on Jan. 14, 2011, the disclosures of which are incorporated herein by reference in their entirety.

FIELD OF THE INVENTION

The present invention relates to the field of robotic systems for use in minimally invasive surgical and diagnostic procedures, especially for use in performing cranial neurosurgery.

BACKGROUND OF THE INVENTION

As of today, brain surgeries remain complex and risky. Conventional open skull surgery is traumatic, may have debilitating side effects to the patient and generally requires long recovery time. The time taken to perform the surgery may be tedious and decreases the efficiency of the medical staff. The complexity of the operations often prevents repeatability if required. The operation itself may cause a brain-shift, and for operations such as tumor resection, the original position of the tumor may be dislocated so that pre-operative planning may no longer be accurate intraoperatively.

There therefore exists a need for a minimally-invasive and automated procedure, which overcomes at least some of the disadvantages of prior art procedures, in particular, in avoiding major trauma to the brain in areas other than that to be operated on, and in doing so, avoiding significant brain-shift, such that the pre-operative planning is still valid intra-operatively.

The disclosures of each of the publications mentioned in this specification, are hereby incorporated by reference, each in its entirety.

SUMMARY OF THE INVENTION

The present disclosure describes new exemplary automated robot-based platforms for minimally-invasive neurosurgical use, including procedures such as resection of brain tumors or the extraction of multiple biopsy samples from large volumes of the brain, or others. Unlike other existing robotic approaches that mimic the surgeon's hand motion, and which therefore generally require substantive access to the operation region, the presently described technology uses the unique capabilities of robotic systems for minimally invasive access to regions of the brain with minimal collateral tissue damage, on the basis of predetermined motion of the robotic actuator holding the surgical tool, which is accurately positioned and moved by the robotic control. The region of the brain to be treated is first mapped using an imaging modality such as CT, MRI or Ultrasound. Based on these images, the surgeon decides on the best path to reach the tumor, if that is the target of the procedure, with minimal trauma to surrounding brain tissue. Minimization of such trauma is important in reducing brain shift, thereby maintaining the spatial accuracy of the preoperative images.

Some prior art robotic systems for neurosurgery, such as the NeuroMate supplied by Renishaw plc of Wotton-under-Edge, Gloucestershire, U.K., access the brain along one trajectory line and can make a procedure such as a biopsy, or a DBS only along that line. The present invention enables access to a larger volume through a single entrance passage. As a result, less brain tissue is damaged during the access process. A small key-hole incision is made in the skull, and a narrow path is traced by the robotic tool to reach the desired location. The robot advantageously consists of a rigid cannulated outer needle with a distally positioned laterally directed hole. A flexible needle is advanced through the bore of the cannulated needle, and delivered to the diseased area through the distal hole. This hole can be angled at any orientation relative to the rigid cannulated outer needle, but optimum access for the flexible needle is achieved if the hole is aligned at right angles to the axis of the outer cannula. The motion of the two needles are computer controlled such that every point in the vicinity of the distal end of the needle can be reached by controlling the insertion depth and the orientation of the rigid needle, and the relative insertion depth of the flexible needle. Using such an arrangement an insertion path width of less than 5 mm is possible. When the desired location is reached, the surgical tool at the end of the flexible needle can be actuated to treat the accessible volume of the tumor. The flexible needle is constructed such that it, or another surgical tool or probe inserted down it, more can perform physical cutting operations, or can deliver an electric current, ablative or photo-therapeutic heat or light, or ultrasound energy to treat, for instance, a tumor, or can incorporate a miniature camera to image the region of interest. For drug delivery the internal flexible needle can be cannulated. For biopsies the needle may be constructed to extract tissue samples. By this means, multiple samples over a large volume to be inspected, can be taken using only one small incision. Access to regions of the brain beyond the operational access of the flexible needle end in a single extension can be reached by withdrawing the flexible needle to within the rigid cannulated needle, and then withdrawing the rigid cannulated needle somewhat, or inserting it further, in order to reposition it to provide access by the inner flexible needle to the new region to be accessed, whether into a deeper or a less deep region of the brain, and at whatever azimuthal angle is needed relative to the first treatment performed.

The needle motion can be controlled in two modes:

1. Based on pre-operative planning, whereby the shape and position of the diseased area is known from preoperative images, and hence the motion needed to reach specific points within the diseased area is known. This mode will require a registration procedure to be performed, generally using markers having known positions and visible in the preoperative images, in order to relate the robotic co-ordinate system to the co-ordinate system of the images. Alternatively, registration can be achieved by surface matching techniques, whereby an intra-operative scan of the subject's head, including at least some anatomic features such as the subject's facial features, and some known features of the mounted robot, is compared with a preoperative scan of the subject's head. Matching of the anatomical features then enables the position of the robot to be determined relative to the preoperative images.
2. Real time control using an external or internal imaging system, such as MRI, CT, ultrasound, or needle mounted sensors. The latter option may use optical, electrical or ultrasound sensors, mounted on either or both the flexible needle and the external rigid needle. Such needle mounted sensors can then be used to detect not only the position of the needle tip, but also to provide data regarding the physiological state and condition of the surrounding tissue.

As an alternative to use of the base element fixed directly to the skull, it is possible to use any of the conventional mounting hardware such as a stereotactic frame in order to attach the needle assembly in a predetermined position to the patient's skull. In such a case, prior art methods can be used to determine the direction of penetration of the treatment needle. In such prior art methods, the region to be treated is defined on preoperative images, which include the mounting hardware used to support the needle insertion device, and the position of the device relative to the mounting hardware is known, such that the device is registered to the preoperative images. The surgeon then defines the orientation angles and depth of penetration of the needle, using the alignment facilities provided on the mounting hardware. Using prior art methods of a single needle inserted straight into the patient's brain, there may be situations where access to the target point is problematic because of sensitive or damage prone regions of the brain in the direct linear access path. Use of the present device enables access to be achieved along a singly articulated path without encountering the sensitive or damage-prone regions of the brain.

Additionally, if adjustable mounting hardware is used, it is possible to access in two dimensions, locations which would otherwise be problematic to reach by a direct linear path. The specific target area is reached by first aligning the device using the mounting frame adjustments, and then a controlled sequential combination of (i) the depth of entry of the cannulated needle and then (ii) the extension of the flexible needle, to reach the target area.

The surgeon can at any time, take active control of the robot and change the operation plan if necessary.

The small access path minimizes brain shift during the surgery and improves operation accuracy and reduces morbidity. This technology allows the robot to reach more areas in the brain from a single cranial incision than previously possible, and opens new horizons in treating brain tumors.

In US Patent Application Publication No. 2009/0048610 to G. Tolkowsky et al., for "Medical Probe Introducer" there is described a hand operated mechanical system for inserting a probe into the subject's cranial tissue, in which the off axis target of the probe or the treatment is reached, either by a use of a straight needle with an angled treatment outlet, or by use of a needle constructed of a shape memory alloy, which bends on exiting its outer cannula in order for the tip to reach the treatment area. However, the need for such a shape memory needle to traverse a curved path on exiting its outer cannula introduces levels of accuracy which may be problematic for such treatments, since unlike a straight needle, it is not clear that the tip will proceed in an arcuate path to its intended target. Additionally, a curved path may aggravate the problem of brain-shift. Furthermore, the system described therein is micrometer based, such that it is slow, and depends on the settings adjusted by the surgeon for accuracy of insertion.

In US Patent Application Publication No. US 2004/0059260 to C. L. Truwit, for "Method and Device for Deflecting a Probe", there is described a method and device for inserting a flexible needle down a cannula having an off-axis exit aperture, such that as it exits from the cannula, the needle can access a region off-axis from the region to which the straight cannula can reach.

However, in neither of these publications is reference made to the question of the mechanical properties of the materials of the flexible needle, and the required shape of a flexible needle in order for it to achieve its aim. There are two conflicting requirements for a neurosurgical device of the type described in this disclosure. In the first place, the outer diameter of the external cannular needle should be as small as possible in order to reduce trauma to healthy brain tissue to a minimum. Ideally, as previously mentioned, an outer diameter as small as 4 mm is desirable, which means that its inner diameter will be of the order of 3 mm. However, the outer diameter of a useful flexible needle incorporating a surgical tool or having a probe or sensor threaded through it, for performing the required operative or therapeutic procedure, should be of the order of no less than 3 mm. Thus, the inner flexible needle has the severe requirement of having an outer diameter of the order of 3 mm., and yet having the ability to make a 90° bend with a radius of curvature of no more than 3 mm, since the exit aperture path should be contained within the outer cannula external diameter limits, as otherwise, it would interfere with the smooth initial insertion of the outer cannula into the brain tissue. Furthermore, after achieving this bend, the flexible needle should be sufficiently strong to be capable of penetrating brain tissue, to withstand lateral forces due to anisotropic nature of the brain tissue, to deploy in a straight line to reach the desired target region with the accuracy required, and to support any axial force which may be required for it to perform its surgical or therapeutic function, or which may be operative on it while moving through the brain tissue. These conflicting requirements mandate novel and inventive configurations of the system and of the flexible needle.

In this disclosure four different solutions are proposed in order to achieve these objectives, as follows:
(a) Use of thin-wall tube structural buckling, where a change in shape of the flexible needle occurs while negotiating the turn, restoring to original shape as it exits the turn. Analysis of such tube buckling under pure bending and optimum shapes of the flexible needle for the purposes of this application are described in the detailed description section hereinbelow.
(b) A hollow chain of magnetic beads, separated from each other at the bend and rejoined upon exit. A quasi-static analysis of magnetic bead chain and some examples are described in the detailed description section hereinbelow.
(c) Use of an annular balloon structure, which is sufficiently pressurized and yet sufficiently flexible that after negotiation of the curve, it maintains its original resistance to axial and lateral forces.
(d) Use of tensegrity structures. A tensegrity structure can be locally un-deployed and weakened in order to negotiate the turn, yet become fully deployed at its full structural strength upon exit. A fuller description of this solution is detailed description section hereinbelow.

There is thus provided in accordance with an exemplary implementation of the devices described in this disclosure, a robotic device for performing an intracranial procedure at a target region of a subject's brain, comprising:
(i) a baseplate adapted for mounting on the skull of a subject,
(ii) a rotatable element disposed on the baseplate, and having an opening in its central region,
(iii) a cannula mounted on the rotatable element coaxially with the opening, and which rotates with rotation of the rotatable element, the cannula being robotically controlled to provide motion into and out of the skull of the subject, and (iv) a flexible needle disposed in the cannula, the flexible needle being controlled to provide motion into and out of a non-axial aperture in the distal part of the cannula, and having a structure adapted to enable it to exit the non-axial aperture and to continue the motion out of the aperture to the target region without losing its mechanical properties, wherein coordinated control of the insertion motion of the cannula and the flexible needle and rotation of the rotatable element enables access to be obtained by the flexible needle to the target region of the brain.

In such a robotic device, the non-axial aperture may comprise a curved section of the cannula, exiting the cannula at right angles to the axis of the cannula, and having a radius of curvature no more than 25% larger than the external diameter of the cannula.

The flexible needle may comprise a thin-wall tube having an oval shape with its shorter dimension being in the same plane as that including the axis of the cannula and the non-axial aperture, or a thin-wall tube having a toroidal shape with its shorter dimension being in the same plane as that including the axis of the cannula and the non-axial aperture.

In alternative implementations, the flexible needle may comprise a hollow chain of magnetized beads, which should be magnetized in a direction such that they are attracted in a self-centering stack. Alternatively, the flexible needle may comprise an annular inflated balloon, or an elongated tensegrity structure. In any of these robotic devices, the flexible needle advantageously may have an outer diameter of less than 4 mm.

Additional implementations can include such a robotic device in which the device is adapted to provide access to the target region of the brain with any collateral trauma to non-accessed parts of the brain being approximately confined to a region having the width of the cannula.

Furthermore, the device could be such that coordinated control of the insertion motion of the cannula and flexible needles and rotation of the rotatable element enables access to be obtained by the flexible needle to the target region of the brain along an articulated path selected to avoid damage-prone regions of the brain. The flexible needle may comprise a cutting tool, such that resection of a brain tumor can be performed with collateral trauma to those parts of the brain not being treated being approximately confined to a region having the width of the first cannulated needle.

Yet other implementations may involve a robotic device of the type described hereinabove, wherein the flexible needle is adapted to be connected to an energy delivery system, such that ablation or optical or electro-treatment of a brain tumor can be performed with collateral trauma to those parts of the brain not being treated being approximately confined to a region having the width of the first cannulated needle. Such a flexible needle may comprise an optical fiber for delivery of the energy.

Additional implementations can include a robotic device in which the flexible needle may comprise a biopsy tool, such that biopsy samples may be obtained from regions of the brain at different positions laterally displaced from each other by distances substantially larger than the width of the first cannulated needle, with collateral trauma to those parts of the brain not being accessed being approximately confined to a region having the width of the first cannulated needle. Alternatively, the flexible needle may comprise a drug delivery passage.

Further example implementations may involve a robotic device further comprising a set of preoperatively inserted markers for relating the position of the robotic device to the skull of a subject, such that the co-ordinate system of the robotic device can be registered to a preoperative image of the skull of the subject. Alternatively, the robotic device may further comprise at least one position sensor disposed in the distal region of the flexible needle, such that the real time position of the flexible needle tip can be monitored intraoperatively, or in the distal region of the cannula, such that the real time position of the tip of the cannula can be monitored intraoperatively.

Yet other implementations perform a method of performing intracranial procedures, comprising:
(i) providing a baseplate and mounting it on the skull of a subject, the baseplate having disposed on it a rotatable element with an opening in its central region,
(ii) mounting on the rotatable element, coaxially with the opening, an assembly comprising:
    (a) a cannula which rotates with rotation of the rotatable element, the cannula being robotically controlled to provide motion into and out of the skull of the subject, and
    (b) a flexible needle disposed in the cannula, the flexible needle being controlled to provide motion into and out of a non-axial aperture in the distal part of the cannula, and
(iii) coordinating the rotation of the rotatable element and the sequential insertion of the cannula and the flexible needle to enable access to be obtained by the flexible needle to a target region of the brain where the procedure is to be performed.

Alternative implementations involve a method of performing neurosurgical procedures at a target region of the brain, comprising:
(i) attaching in a predetermined orientation and position on the skull of a subject, a base element,
(ii) mounting on the base element, an assembly comprising:
    (a) a cannula, the cannula having a non-axial aperture in its distal part, and a motion controller to provide motion into and out of the skull of the subject, and
    (b) a flexible needle disposed in the cannula, the flexible needle having a motion controller to provide motion into and out of the non-axial aperture in the distal part of the cannula,
(iii) selecting on a preoperative image of the brain, a singly articulated path avoiding damage-prone regions of the brain, and
(iv) controlling the sequential insertion motion of the cannula and the flexible needle to enable access to be obtained by the flexible needle to the target region of the brain along the singly articulated path.

In either of these methods, the flexible needle may be a thin-wall tube having an oval or a toroidal shape, or any of a hollow chain of magnetized beads, an annular inflated balloon, or an elongated tensegrity structure.

It is to be understood that the term flexible needle, as used and as claimed in the present application is intended to apply to the element inserted through the bore of the external rigid cannula, whether that element is a full needle, such as for delivering a biopsy harvesting tool, or a sensor or an electrode, or the like, or whether that needle is hollow, such as for drug delivery, or for extracting a fluid sample, or the like.

BRIEF DESCRIPTION OF THE DRAWINGS

The invention will be understood and appreciated more fully from the following detailed description, taken in conjunction with the drawings in which:

FIG. 9 illustrates schematically a complete practical robotic system based on the systems shown in the above Figures.

DETAILED DESCRIPTION OF THE INVENTION

Figures 1A, 1B:
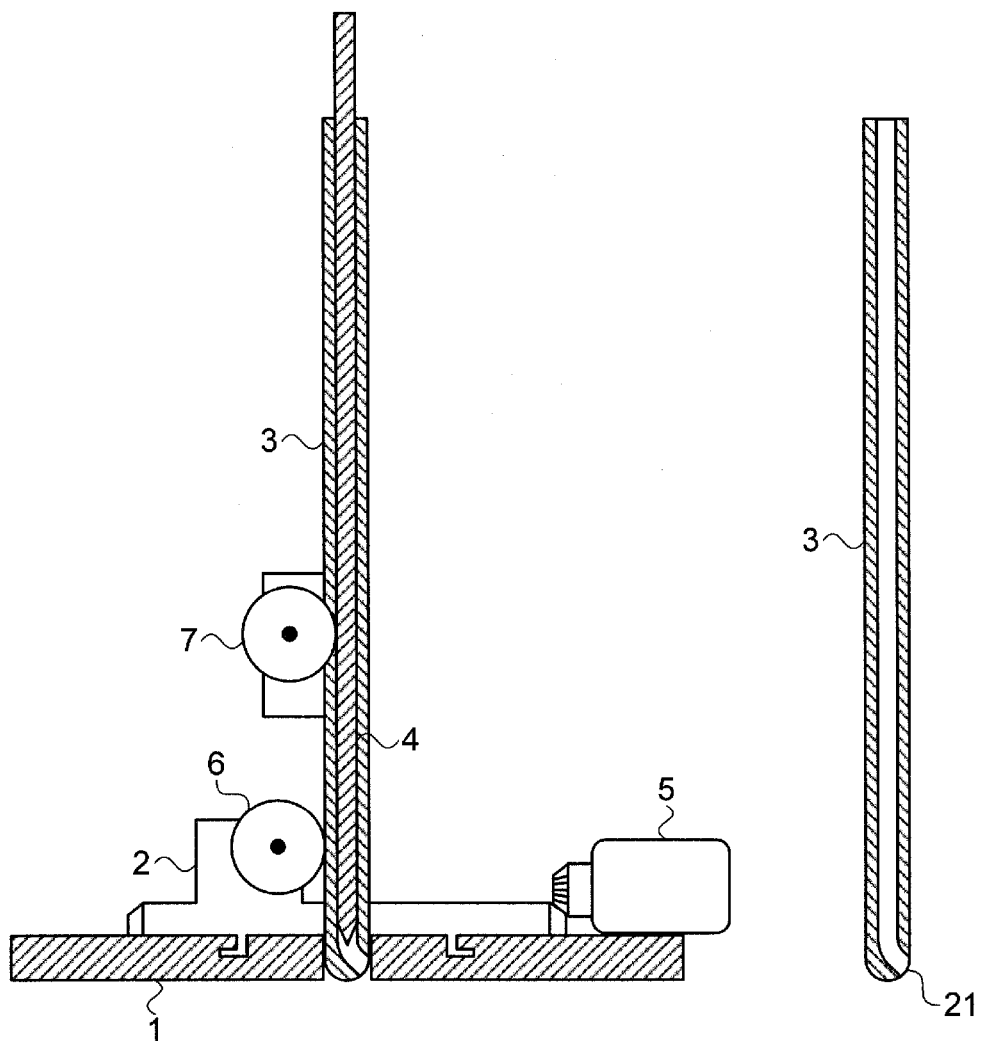
FIGS. 1A and 1B illustrate schematically an exemplary implementation of a robotically controlled neurosurgical apparatus using a double cannulated needle assembly, as described in this disclosure.

Reference is now made to FIGS. 1A and 1B, which illustrate schematically an exemplary implementation of a robotically controlled neurosurgical apparatus according to the novel designs presented in this disclosure. A central feature of this neurosurgical robot implementation is a combination of a flexible needle 4 which can be controllably inserted into an external rigid cannular needle 3. Although the flexible needle is shown in the drawings of this disclosure as a solid needle, it can, as previously mentioned, be either solid or cannulated. The shape of the external rigid needle is shown in FIG. 1B. At its distal tip 21, the bore of the external needle is diverted laterally, so that the distal opening is directed sideways from the bore of the needle, at an angle to the axis of the bore of the needle. In FIGS. 1A and 1B, the exit angle is shown as approximately 45° to the cannula axis, though it is to be understood that this angle can be selected to enable ease of passage of the flexible needle around the bend of the bore, depending on the flexibility and diameter of the flexible needle 4. The external needle should advantageously be made of a rigid metal, which should not be a ferromagnetic metal if an MRI system is to be used for the intraoperative real-time imaging. The internal needle may be made of a flexible metal such as Nitinol, or, if the stresses to be applied to it are not excessive, of a plastic material, the level of flexibility being such that it can negotiate the bend at the tip of the external needle while maintaining its shape after leaving the lateral hole of the external needle.

As shown in the exemplary robot of FIG. 1A, the combination of internal and external needles are mounted above an opening in a base section 2, which itself is rotatably mounted on a main base 1. Rotation of the base section 2 around the main base 1 may be performed by means of a robotic actuation motor 5, which should also include an angular position encoder, so that the angular orientation of the base section 2 is known. Correct rotation of the base section 2 relative to the opening in the base section should be ensured, such as by means of a circular slide and guide arrangement, as shown on the top surface of the main base 1. It is also important that the external cannula 3 and its contents rotates in exact unison with the base, since otherwise, the base encoder would give incorrect readings for the angular position of the needle assembly. This can be achieved either by ensuring that the rotary friction of the external needle with the rotating base is much higher than the expected friction force between the brain tissue and the needle after insertion, or by provision of a mechanism to positively fix the angular position of the needle assembly to the base, such as a key-way running down the length of the outer wall of the cannulated needle such that it can slide relative to the rotating base, but cannot rotate independently thereof.

The insertion of the internal flexible needle within the external needle may be controlled by means of a robotic motor and encoder 7, as shown in FIG. 1A, or by means of a linear motor (not shown). If a rotary drive is used, access to the flexible needle 4 can be obtained by means of a slot in the external cannula wall. Alternatively, the inner flexible needle 4 can be moved from its proximal end section protruding from the external cannula 3. The linear insertion and extraction motion of the complete double needle assembly relative to the base plate may be controlled by means of another motor and encoder 6. If the system is to be used with MRI intraoperative imaging, linear or rotary piezoelectric motors may advantageously be used to provide the motion.

Figure 2:
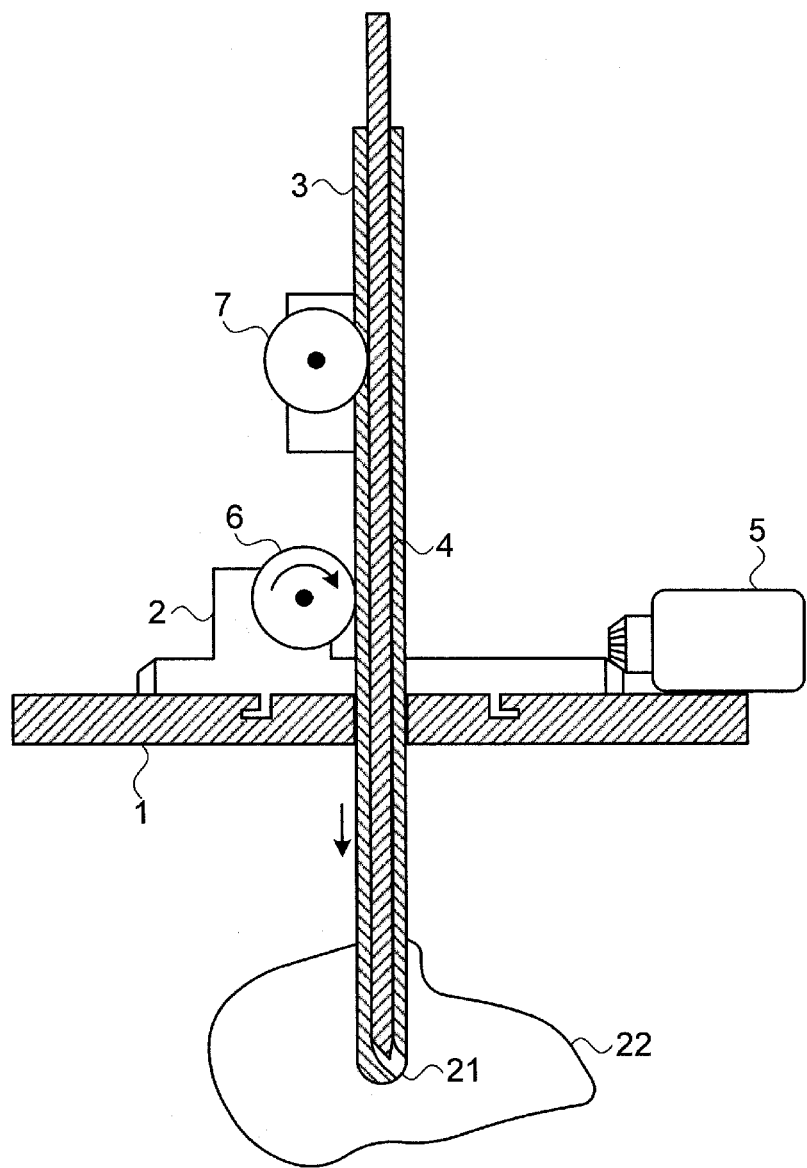
FIG. 2 illustrates schematically how the complete double needle assembly of FIG. 1A can be advanced through the holes in the base sections of the device, using a motor-encoder assembly.

Reference is now made to FIG. 2, which illustrates schematically how the complete double needle assembly 3, 4, can be advanced through the holes in the base sections, using the motor-encoder assembly 6, until the distal tip of the assembly has accessed the region 22 of the brain which it is desired to treat.

Figure 3:
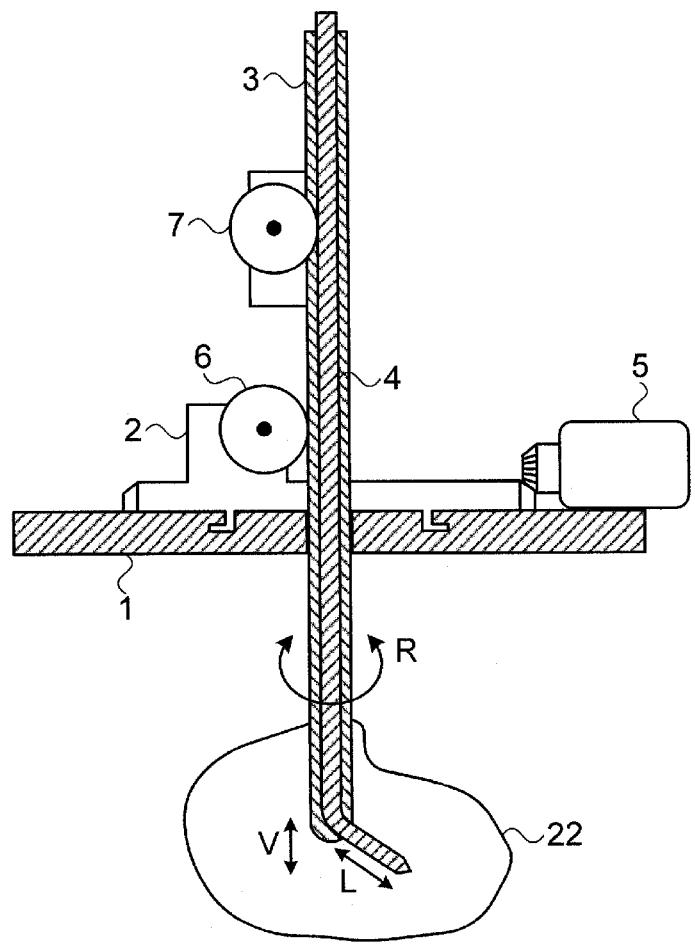
FIG. 3 illustrates schematically how the internal flexible needle of the assembly of FIG. 2 can be advanced outside of the external rigid needle, so that its tip can reach the regions of the brain which it is desired to treat.

Reference is now made to FIG. 3, which illustrates schematically how, once the combined needle assembly 3-4 has been rotated so that the distal opening 21 in the cannulated needle is orientated within the region 22 of the brain to the first part to be treated, the internal flexible needle 4 can be advanced outside of the external rigid needle 3, using the motor-encoder 7, so that the tip of the internal flexible needle can reach that part of the regions the brain which it is desired to treat. Since in the implementation shown in FIGS. 1 to 3, the exit angle of the internal needle is fixed, the combined motion of all three motors is necessary in order to provide access to any part of the entire volume of the region to be treated. Thus, combined activation of the motor 6 to drive the depth of penetration of the external needle 3, and the motor 7 to drive the extent of the lateral extension of the internal needle 4 from the exit of the external needle, enables the full two-dimensional area shown in the drawings to be accessed. The vertical arrow marked V indicates the motion direction enabled by insertion and withdrawal of the external annular needle 3, and the angled arrow marked L indicates the direction of the longitudinal extension motion of the inner flexible needle 4, to access the off-axis region of the brain which it is desired to treat. In order to provide access to any part of the entire three-dimensional volume of the region to be treated, i.e. including cross-sections out of the plane of the drawing, it is necessary to activate motor 5 in order to rotate the complete combined needle assembly by rotating base section 2, as indicated by the rotation arrows, marked R in FIG. 3. The robotic control system, using the dimensional extent of the region to be treated as determined by the preoperative three-dimensional images generated of the region, coordinates motion of all three motors in order to gain access to any part of the entire three-dimensional volume. Thus, a specific target area is reached by combination of (i) the orientation angle of the cannulated needle 3, such that its distal opening is directed towards the target area, (ii) the depth of entry of the cannulated needle 3, and then (iii) the extension of the flexible needle 4, to reach the target area.

In FIG. 1A to 3, and the corresponding FIG. 5 later in the disclosure, the base section 2 is shown as a large baseplate covering much of the extent of the main base 1. However, it is to be understood that the so-called base section through which the internal and external needle assembly is axially mounted and rotates therewith, may be no more than a collar mounted on the external needle assembly, with a robotic mechanism for rotating the collar relative to the main base fixed to the subject's skull. The invention is not therefore intended to be limited by the type of rotating base section shown in FIG. 1A, the operational feature being that that element be capable of controllably rotating the needle assembly around its axis.

Figure 4A:
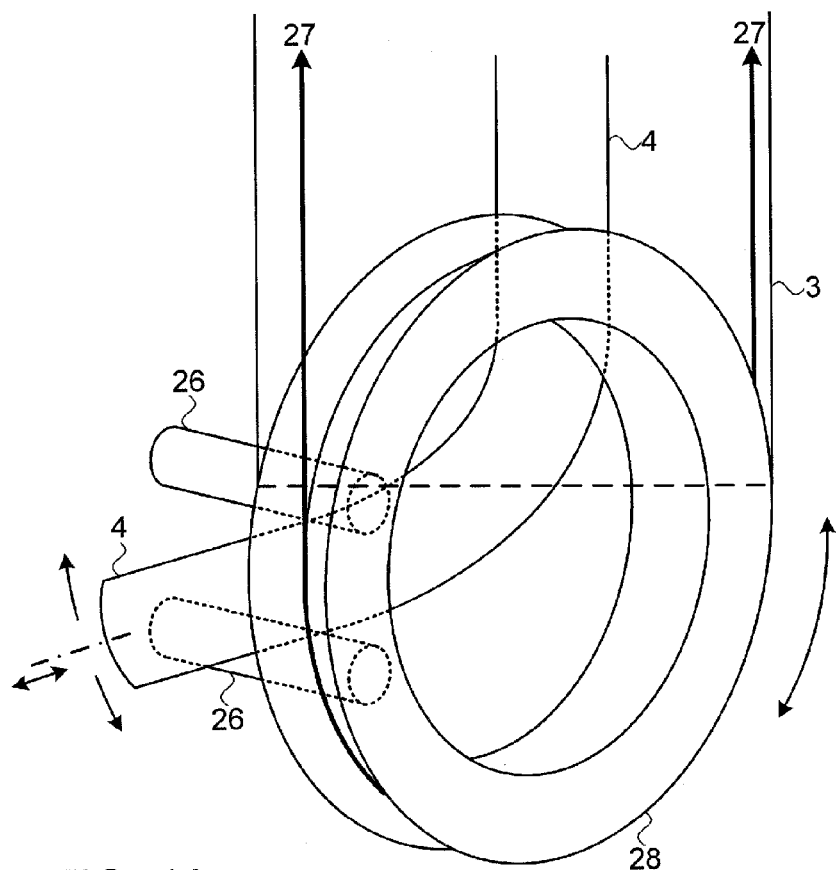
FIGS. 4A and 4B illustrate alternative methods to that of FIG. 3, of enabling the tip of the internal needle to reach any part of the region to be treated.

As an alternative to accessing the lateral (longitudinal) extent of the volume to be treated by means of the extension of the internal needle 4 through a fixed angle exit port in the outer rigid cannular needle 3, it is possible to direct the angle at which the inner flexible needle is extended into the cerebral tissue, by means of an adjustable angle exit port incorporated into the external rigid cannula. One such implementation is shown in FIG. 4A, which is an enlarged isometric drawing of the bottom end of the double needle assembly. According to this implementation, the bottom end of the external cannular needle 3 is provided with a variable angle exit aperture, through which the internal flexible needle 4 can protrude. This exit aperture can be in the form of a pair of pins 26 attached to a rotatable pulley 28. The pins act as jaws which constrain the outer surface of the internal needle 4, and direct it to the desired angle as the pulley 28 is rotated. The angle of the exit aperture can be conveniently be adjusted for instance by means of a pair of drive wires 27 looped around the pulley 28. The outer cannula 3 should be extended to cover the outer diameter of the pulley wheel and to enclose its distal end, to ensure smooth insertion of the device, without the pulley wheel or its pins causing unnecessary damage to the cerebral tissue. A slit can be formed in the rounded distal cover of the pulley wheel to enable the inner flexible needle to exit the cover at the desired angle, In use, the robotic device should be inserted into the subject's cerebral tissue with the pulley positioned such that the pins are in their lowermost position (in the sense of the directions shown in the drawing), in line with the axis of the external cannula, and with the inner flexible needle extended far enough for its distal end to just be captured between the pins. The pulley may then be rotated until the pins and the tip of the internal flexible needle held within the confines of the pins are rotated to such an angle that the flexible needle is directed to extend in the direction predetermined to reach the intended target region. Once this angular orientation has been achieved, the inner flexible needle can be extended outwards from the outer rigid cannula, to access the region to be treated, As an alternative to a pulley wire with pins, reference is now made to FIG. 4B which illustrates a rotatable block 30 with a channel 31 formed therein mounted within the distal end of the outer cannulated needle 3. The inner flexible needle 4 can be guided into the channel 31 while it is aligned axially with the bore of the cannulated needle, and the block can then be robotically oriented to the desired angle required to direct the internal flexible needle to the desired point in the subject's brain. The center of rotation of the guide block 30 should be near its proximal end so that the entrance to the channel 31 remains fairly centrally located within the cannulated needle 3, to enable smooth entry of the flexible needle 4. The robotically controlled drive motor for pulling the pulley wires to adjust the angle of this exit aperture, or to rotate the angularly variable channel block, can then be used in lieu of, or in addition to, the drive motor 6 for inserting the external cannula, while performing the surgical procedure. By this means additional flexibility or additional simplicity, is available for gaining access to perform the procedure. Thus for instance, the external cannular motor 6 can be used for advancing the operating end to the most proximal point of the region to be treated, and the treatment itself performed by means of the variable angular exit aperture of the internal needle and the exposure extent of the internal needle, as shown by the set of arrows at the tip of the internal flexible needle, together with, of course azimuthal rotation of the entire robot activation arm. According to this implementation, with the tip of the external cannular needle at the top of the treatment region, the pulley needs to cover an angular range sufficient for covering the entire region to be treated.

Figure 4B:
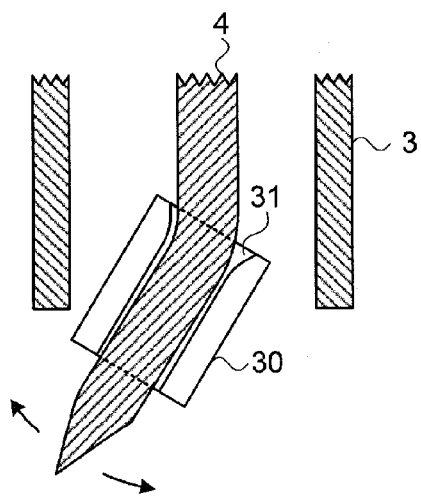

The implementations of FIGS. 4A and 4B are illustrated using a pulley wheel with wires operated externally to rotate it, since such an arrangement can be readily installed within the confines of the cannular needle 3, but it is to be understood that any other form of rotation that does not unduly increase the outer diameter of the device can alternatively be used.

The angle though which the flexible needle can be delivered, whether use is made of the fixed angle exit port of FIGS. 1 to 3, or the variable angle exit port of FIG. 4, is dependent upon the flexibility of the inner needle and on its diameter. The more flexible the needle, the greater the angle that can be negotiated, and the thinner the needle, the greater the angle that can be negotiated. A compromise must be made between the need to maintain sufficient stiffness in the flexible inner needle to enable it to reach its planned target without being deflected, and the need for it to readily deploy from the angled outlet port at the end of the rigid outer cannula. Because of the complexity of the arrangements shown in FIGS. 4A and 4B, it is likely that they will only be implementable for use with fine inner needles or probes.

As mentioned in the summary section hereinabove, a number of novel configurations are now described for a flexible needle which can be exited through a 90° angle bend from the inner cannula, through a radius of curvature of the same order of magnitude as the effective diameter of the needle itself, without suffering any irreversible buckling damage as a result of the bend. A typical requirement for the strength of such a needle for use in cranial treatments is that a 5 gm. lateral force applied on a 30 mm length of the flexible needle would not result in a deflection of more than 1 mm.

It is known that when a thin-wall circular cylindrical tube, such as the flexible needle of the present system, is subjected to pure bending, its cross section becomes more oval as the radius of curvature decreases. Ovalization growth causes a progressive reduction in the shell's bending rigidity. Eventually, a maximum value of stress is reached and further bending results in plastic deformation of the tube. Once this point has been reached, the needle no longer behaves elastically, and cannot therefore be used in order to deploy correctly out of the outer cannula. In order to reduce the radius of curvature through which a tube can bend and even locally buckle before crossing the elastic limit, a needle having an initial elongated cross-sectional shape perpendicular to the plane of bending is used.

Figure 5A:
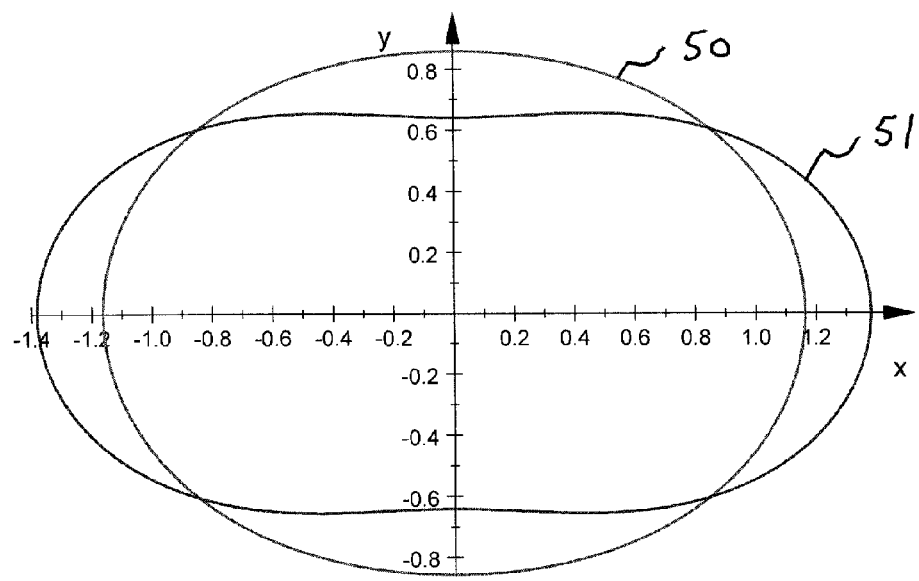
FIGS. 5A and 5B illustrate schematically the cross section of two types of oval shaped needles, according to an implementation of flexible needles for use in the systems described in FIGS. 1 to 4B.

Reference is now made to FIG. 5A, which illustrates schematically the cross section of an oval shaped needle, according to a first implementation of a method of providing a flexible needle that will negotiate a radius of curvature of the same order of magnitude as the effective diameter of the needle itself, more readily than a needle having a circular cross-section. The axes are labeled in millimeters, showing the overall maximum diameter of approximately 3 mm. Two oval shaped needles are shown in FIG. 5A, one 50 having an ellipsoidal shape, and the other 51, having a toroidal shape. These two shapes are bistable conditions of the tube as it bends, switching between the oval and the toroidal cross section reversibly. However, it is to be understood that a toriodal cross section needle could also be used as the unstressed profile before bending. Calculations have shown that in order to negotiate a 3 mm radius of curvature without undergoing plastic deformation, a stainless steel toroidal shaped needle having a width of 3 mm should have a wall thickness considerably less than the wall thickness of standard hypodermic needles. Such a needle does have sufficient mechanical strength to be used for cranial use, and still provide the required 1 mm accuracy at a distance, 30 mm from the exit aperture of the outer cannula.

Figure 5B:
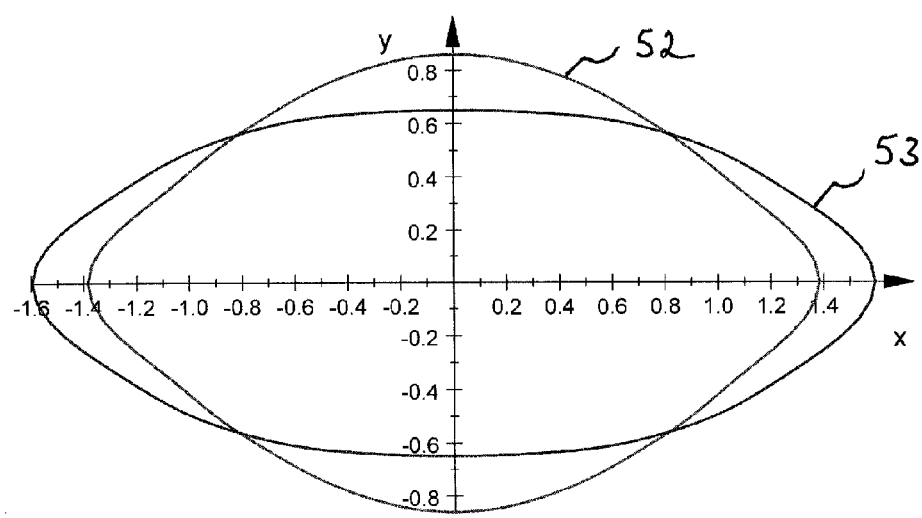
Figure 5:
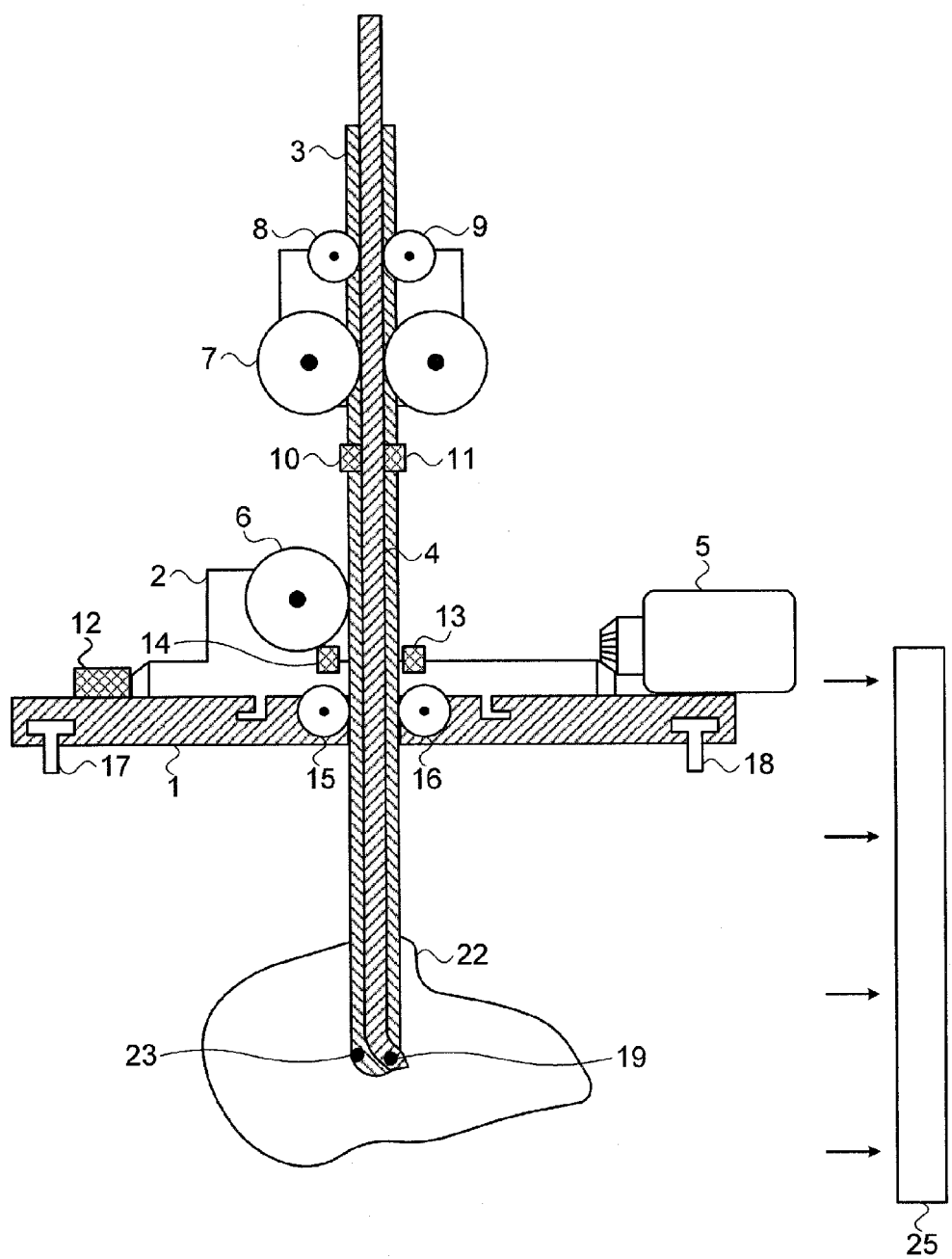

Reference is now made to FIG. 5B, which illustrates schematically an alternative flattened profile needle, which also provides satisfactory properties for use in the cranial treatment devices of the present disclosure. The profile shown in FIG. 5B is that of an eye shape 52, showing the ovalization effect 53 taking place on bending. As the needle bends, it switches at the predetermined stress point, between the two bi-stable shapes, and returns on becoming unbent. It can be shown that the critical moment before plastic deformation occurs is slightly lower than that of the oval or toriodal shapes of FIG. 5A.

Figure 6:
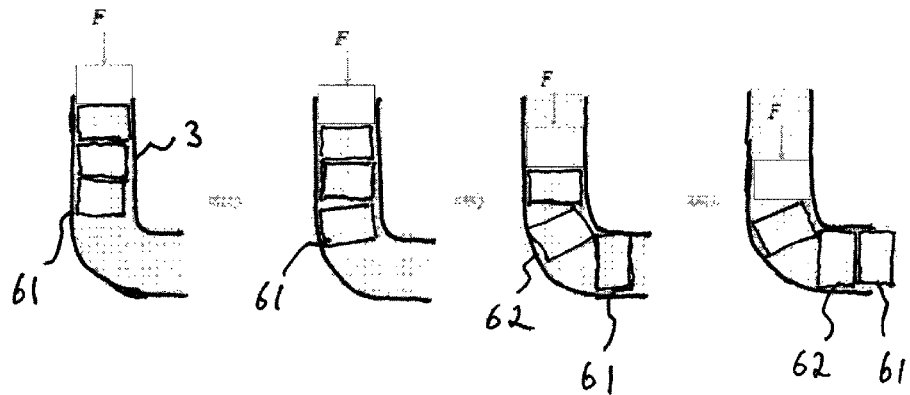
FIG. 6 illustrates schematically another flexible needle implementation constructed as a passive magnetic bead chain.

Reference is now made to FIG. 6, which illustrates schematically another implementation by which a flexible needle for use in the present device can be constructed as a passive magnetic bead chain, made up of a stack of magnetized beads. The magnetic chain is hollow, enabling passage of the detection and treatment tools as required. FIG. 6 shows a sequence of drawings as the bead chain is pushed into the outer cannula 3 by the eternally applied force F until it meets the 90 degree exit aperture curve, as illustrated in FIG. 6. The front most bead 61 is then partially separated from the adjacent bead and moves forward into the curve. The next beads 62 follows it and after exiting the curve, the beads are reattached due to the magnetic force between them, to form the original rigid beam structure. The magnetic forces acting are such as to make the separate beads making up the chain self-centering. This passive magnetic bead chain therefore fulfills the requirements for use in the present device, since on one hand, the bead chain becomes loose while going through the curve, thereby enabling each bead to negotiate the curve individually, while on the other hand, the bead chain maintains lateral strength when it protrudes from the output cannula, enabling it to sustain the external loads.

An example bead chain was constructed to verify firstly that the chain of this implementation can endure the 90 degree bend of the external cannula; and secondly that a load bearing test verifies that the chain is strong enough upon exit from the external needle to fulfill the needs of the cranial procedures envisaged using this device. An exemplary chain of 15 hollow magnetic beads made of a neodymium rare earth magnetic material $Nd_2Fe_{14}B$ was evaluated. The typical magnetism of this material is approximately 1,000 kA/m. Bead dimensions were: outer diameter of 3 mm, inner diameter of 1 mm and height of 2 mm, resulting in a magnetic moment of m≈50 $Am^2$. Two channels were examined, with internal diameters of ~3 mm and 3.3 mm, and in both cases, the beads successfully negotiate the curve, though in a slightly different manner.

In order to perform his strength test of the magnetic bead chain, the magnetic bead chain was horizontally fixed at one edge and weights were hung on the other edge, at two locations. The chain failed at weights of 12 gr and 8 gr, 2 cm and 2.6 cm from the first bead, respectively. The results of this feasibility trial show that the chain tested is sufficiently rigid to use as a solution for the internal needle, being strong enough and expected to retain the required accuracy level.

Figure 7:
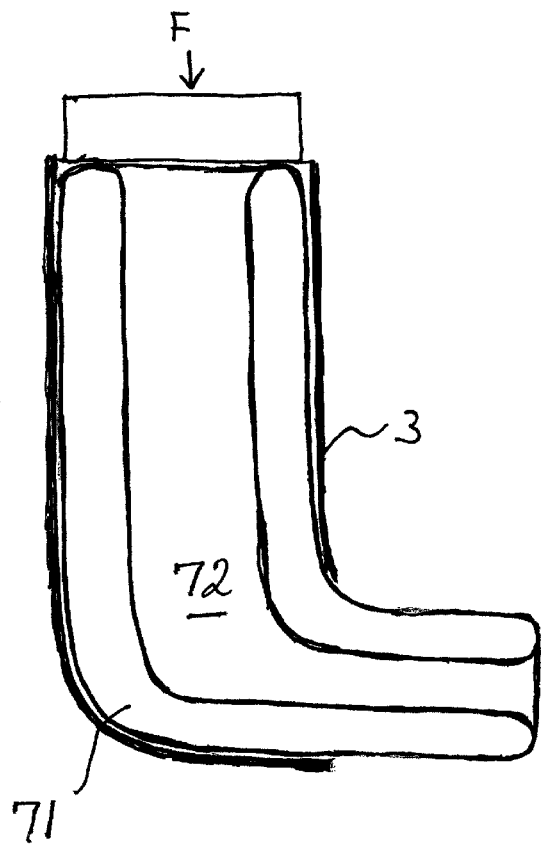
FIG. 7 illustrates a further implementation of the flexible needles for use in the system of the present disclosure, in the form of an inflatable annular shaped balloon.

Reference is now made to FIG. 7 which illustrates a further implementation of the flexible needles for use in the system of the present disclosure, in the form of an inflatable annular shaped balloon 71, negotiating the curve at the exit of the outer cannula 3. The balloon should be constructed of a material sufficiently strong and yet sufficiently flexible to provide the properties required of the inflatable needle. Kevlar is a good candidate for such an inflatable needle balloon. At a sufficiently high filling pressure, the annular balloon has sufficient strength to fulfill the requirements of this application with regard to reaching the target accurately without being deflected by the small lateral forces that may arise during its passage through the brain tissue, yet the high lateral forces exerted on by the exit curve of the outer cannula enable it to bend sufficiently to negotiate the bend. The center of the annular balloon 72 can then be used for passage of a surgical or therapeutic tool or probe.

Figure 8:
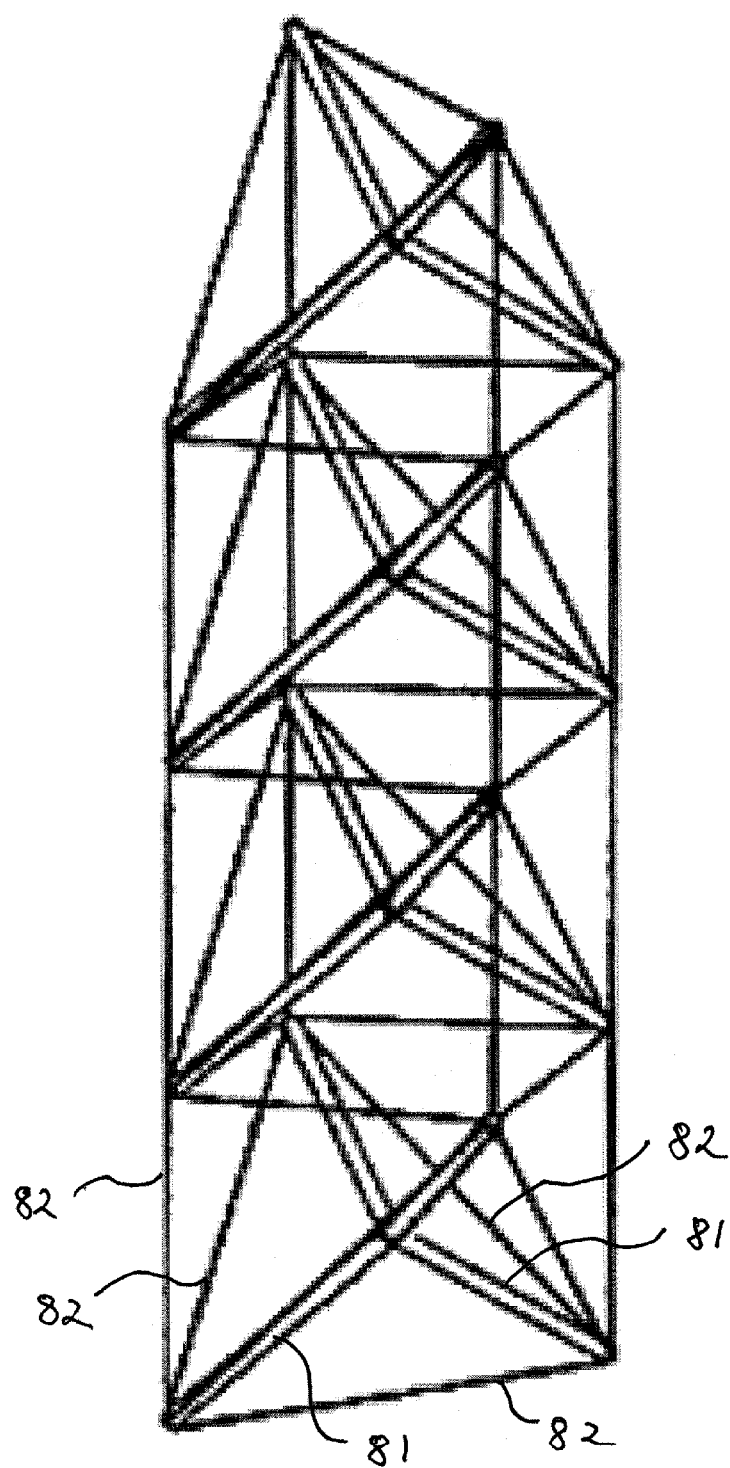
FIG. 8 illustrates a flexible needle construction, utilizing a tensegrity structure to provide the structural strength combined with the required flexibility when negotiating the bend at the exit of the outer cannula.

Reference is now made to FIG. 8, which illustrates yet another "flexible needle" construction, utilizing a tensegrity structure to provide the structural strength combined with the required flexibility when negotiating the bend at the exit of the outer cannula. A tensegrity structure is based on the use of rigid components 81 in compression inside a net of continuous pretensioned cords or wires 82. Deployable tensegrity structures have been widely investigated for use in aerospace applications. Such structures are light weight, yet strong enough due to their special structure. A miniature passive tensegrity mast with similar bi-stable struts using elastic fabric instead of cables as the pretensioned elements for manufacturing simplicity can be used as the "flexible needle" element of the present application.

The tensegrity mast is constructed so that it has good compressive and tensile strength, and a predetermined lateral strength also. The tensegrity structure is subject to two different levels of lateral forces. As the structure progresses through the brain tissue, although the tissue itself presents only a low level of longitudinal resistance to that motion, there may be lateral forces exerted on the mast because of other elements present in the brain, such as blood vessels, which are substantially firmer than the brain tissue itself. Such lack of mechanical isotropy in the tissue may exert lateral forces on the tensegrity structure as it proceeds, and because of the need for accuracy, the structure must be sufficiently strong to withstand such lateral forces with a minimal predetermined deflection. On the other hand, during entry through the bend in the outer cannula, when the leading edge corner strut of the tensegrity mast first impinges on the outer curved wall of the inside of the exit bend of the outer cannula, it undergoes lateral forces of such a level that the structure collapses locally by release of the tension on the connecting wires to that strut, and the mast can begin to negotiate the bend. The structural integrity of the remainder of the structure is unaffected, such that the longitudinal force driving the structure through the curve in the external cannula does not cause collapse elsewhere. As each element passes the beginning of the curvature, it too gives under the lateral forces, retensioning itself as the curve is completed. These lateral forces are substantially higher than the lateral forces exerted by mechanical anisotropy in the brain tissue. The tensegrity structure is constructed with struts and tensioned wires calculated such that its resistance to collapse when lateral forces are applied to it is such that it readily negotiates the curvature of the outer cannula, but has sufficient resistance to maintain its integrity when lateral forces expected from passage through the brain tissue are experienced. Methods of designing and constructing such tensegrity structures are well known in the art, such as in the reference volume by R. E. Skelton et al, entitled "An Introduction to the Mechanics of Tensegrity Structures," in The Mechanical Systems Design Handbook: Modeling, Measurement, and Control, published by CRC Press; III (17) 2001. It is to be understood that in the implementations shown in FIGS. 6 and 8, i.e. the magnetic bead chain and the tensegrity structure, and to a lesser extent, also the annular balloon implementation shown in FIG. 7, the nature of the "flexible needle" is such that it does not itself generally act as the surgical tool element or as the drug delivery conduit, but rather acts as a guide channel reaching the application target region, and that the operative surgical or therapeutic element may be threaded down the "flexible needle" to the target region. However, in some applications, such structures do indeed behave as part of the operative element itself, such as being part of a probe or an electrode, such that the term "flexible needle" is to be understood to be cover all such implementations and uses. It is to be understood that the specific embodiments shown in FIGS. 1 to 8 are only possible examples of how to implement the robotic neurosurgical systems described in the present application, and that they are not intended to limit the scope of the invention of the present application, which is based on the use of a pair of concentric needle elements for accessing the region to be treated, even if in the depth of the brain, by means of a small incision and a narrow access path. The outer one is a rigid guide element and the inner one is a flexible operating element—flexible such that it can be directed out of the inner guide at a desired angle, and an operating element because it is equipped with the desired tool for performing the surgical or diagnostic procedure to be undertaken. Access to any part of the region to be treated is provided by combinations of motion of the inner and outer elements.

Use of the device according to any of the above described implementations, thereby enables the execution of comparatively large volume procedures within the interior of the brain, yet without causing more trauma to the rest of the brain than that of the insertion of the external cannula along its narrow path. Thus, use of the robotic neurosurgical device of the present application, using minimal access from a small burr hole in the skull, enables the treatment of a substantially large volume of the brain with minimal collateral trauma to those parts of the brain not being treated. Furthermore, because of the simplicity of the access method used, the surgeon can choose the access path such that it causes least trauma to the other parts of the brain, even though that path may be longer than the closest path from the skull to the region to be treated.

As previously mentioned, treatment of the desired region can be accomplished either by means of a cutting instrument at the distal end of the internal needle, or by means of an electric current, or by ablation by means of energy delivered down the internal needle, or by means of drug delivery to any or all parts of the region to be treated. Delivery of heat or light can be very advantageously performed using fiber optical delivery, with the optical fiber either replacing the internal needle completely, or being threaded through the internal needle, with its termination at the tip of the internal needle. Additionally, biopsies of any part of the region be treated can be simply executed using biopsy pincers at the end of the internal needle.

Reference is now made to FIG. 9, which illustrates schematically a complete practical robotic system based on the above described implementations, including a number of safety features required by such a system for performing neurosurgery. In the first place, in order to define the position of the robotic system activation arm relative to the position of the region to be treated, as determined from preoperative three-dimensional images, some registration features must be provided. In the presently shown implementation, this is achieved by the provision of preferably three or more pins 17, 18, inserted into the skull preoperatively, such that their position is uniquely defined in the preoperative three-dimensional images. These pins are inserted at positions which are predefined to match the mounting holes in the main base 1 of the robotic system, such that when the system is mounted on these pins, its position is registered relative to the data of the preoperative three-dimensional images. The robotic control commands to the distal end of the internal needle of the activated arm can thus be related to the position of features shown in the preoperative three-dimensional images.

In addition in FIG. 9 there are shown back-up sensors and encoders for every motion function of the robotic system, as required by the safety regulations for use of such systems. Thus for instance the physical position of the internal flexible needle may be determined by primary 10 and secondary 11 encoders, while the electronically determined position of the motor driving the internal flexible needle may be determined by primary 8 and secondary 9 encoders. Additionally, the physical position of the external rigid cannular needle may be determined by primary 13 and secondary 14 encoders, while the electronically determined position of the motor driving the external rigid cannular needle may be determined by primary 15 and secondary 16 encoders. Furthermore an encoder 12 for the rotating platform angular position is also provided. This encoder also generally has a back-up (not shown in FIG. 9). The encoders descried in this disclosure may include optical, magnetic, electrical, or inductive encoders. All of the sensors, motors and encoders are connected to the robotic controller, which, for simplicity, is not shown in FIG. 9.

Additional sensors can be incorporated at the distal end of the flexible needle, to provide additional information or additional guidance to the surgeon. Thus, in FIG. 9, there is shown a representation of an electrophysiological or optical sensor 19, for tissue diagnosis. In addition, an ultrasound sensor can be added, such that it detects the needle location in real time as well as the boundaries of the diseased area. The ultrasound sensor can be located either on the flexible needle 19, or on the external rigid cannula 23. In the latter case the ultrasound sensor can sense both the flexible needle tip as well as the tumor boundaries. It is sufficient to detect only the diseased area boundaries, as the relative position between the flexible needle tip and the rigid needle mounted ultrasound sensor is known from the robot control system. An infra red sensor that can detect and distinguish tissue properties some distance inside a tissue can alternatively be used for this purpose. Such optical sensors can detect, for instance, fluorescence effects in tissues, to label specific types of cell to which the appropriate fluorescing drug attaches. Similarly, an electric sensor that can detect the differences in electric properties between healthy and diseased tissue can be added to the needle tip.

Furthermore, the camera of an imaging system 25 is shown in FIG. 9, such that intraoperative images of at least some of the region 22 of the brain being treated, the needle tips, the main base 1 and its skull locating elements 17, 18, can be obtained, most advantageously together with anatomic features of the subject's skull and/or face. Such images can be used for monitoring the position of the needle tips, and for providing information for performing a registration of the robotic device with the preoperative images available.

Figure 10:
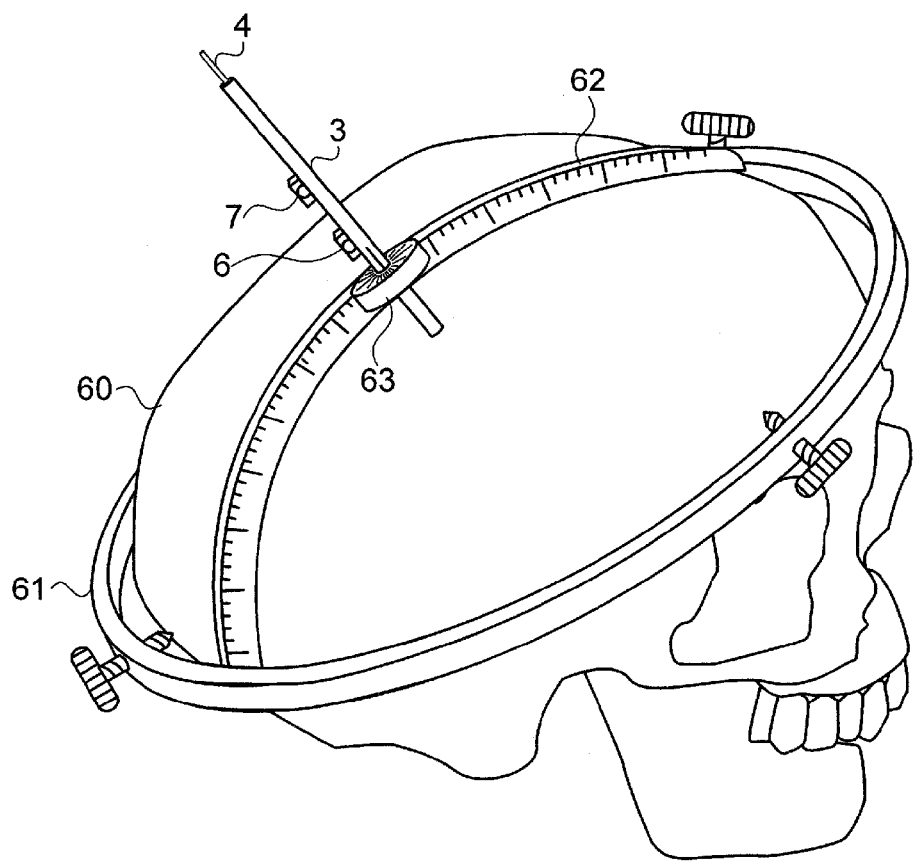
FIG. 10 illustrates schematically further exemplary implementations of needle insertion devices using conventional head clamping devices.

Finally, reference is now made to FIG. 10, which illustrates schematically further exemplary implementations of the needle insertion devices described in this disclosure. In FIG. 6 there is firstly shown an alternative method of fixing the robotic device of the present application to the skull 60 of the patient being treated. This is illustrated in FIG. 6 using a phantom skull only in order to show the fixation method. Instead of being attached by means of a base unit which is screwed directly into the skull of the patient, as is shown in the previous implementations, in FIG. 10, the needle insertion system is supported on a stereotactic frame 61, of any type that is known in the art, though an y other type of frame defining the position of the robotic device relative to the skull may also be used. As an alternative to a stereotactic frame, a Mayfield clamp may alternatively be used, though in this case, there will be need to perform a registration procedure in order to define the position of the clamp and the device attached thereto to the preoperative images, such as by surface feature matching or fiducial markers. In the implementation shown in FIG. 10 the angular alignment scale 62 is shown for only one azimuthal orientation, but it is to be understood that the other two azimuthal orientations also have scales to enable alignment to be made in those angular directions too. The device is attached by means of a rotatable base unit 63, and the needle assembly, 3, 4, with its robotic controls 6, 7 are inserted through this rotatable base assembly in a similar manner as in the previous embodiments of FIGS. 1A to 9.

FIG. 10 also illustrates an alternative use of the device of the present disclosure, to improve prior art methods of determining the direction of penetration of a treatment needle used in neurosurgery. In such a prior art methods, the region to be treated is defined on preoperative images, which include the mounting hardware used to support the needle insertion device. This mounting hardware could be the relevant parts of a stereotactic frame or of a Mayfield clamp. The surgeon then defines the orientation angles and depth of penetration of the needle, using the alignment facilities provided on the mounting hardware. Since the same mounting hardware is registered in the preoperative images, the surgeon can then access the intended target using calculated angles and depths for that mounting hardware. Using prior art methods of a single needle inserted straight into the patient's brain, there may be situations where access to the target point is problematic because of sensitive or damage prone regions of the brain in the direct linear access path.

According to an alternative use of the system of FIG. 10, where a stereotactic frame implementation is illustrated, the same registration procedure can be used as described above, but instead of aligning the prior art linear entry needle directly at the target, the surgeon can use the present device to circumvent any regions on the linear path where access is contraindicated. In use, the surgeon may plan an "articulated" safe entry path, using the pre-operative images. The surgeon then aligns the needle assembly 3, 4, in the correct angular directions, using the head clamp scales 62, and the graduated base scale 63 of the device, and then actuates the entry procedure described above in connection with the embodiments of FIGS. 1A to 9, firstly inserting the external cannular needle 3, using the drive motor 6, and then, deploying the flexible needle 4, using the drive motor 7. As an alternative, a variable opening cannular needle can be used as described in FIGS. 4A and 4B. The device is thus able to access in two dimensions, locations which would otherwise be problematic to reach by a direct linear path. The specific target area is reached by controlled combination of (i) the depth of entry of the cannulated needle 3, and then (ii) the extension of the flexible needle 4, to reach the target area.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A robotic device for performing an intracranial procedure at a target region of a subject's brain, comprising:
    a baseplate adapted for mounting on the skull of a subject;
    a rotatable element disposed on said baseplate, and having an opening in its central region;
    a cannula mounted on said rotatable element coaxially with said opening, and which rotates with rotation of said rotatable element, said cannula being robotically controlled to provide motion into and out of the skull of said subject; and
    a flexible needle having mechanical properties, disposed in said cannula, said flexible needle being controlled to provide motion into and out of a non-axial aperture in the distal part of said cannula, and having a structure adapted to enable said needle to change its shape to exit said non-axial aperture and to continue said motion out of said aperture to said target region while maintaining the shape it possessed prior to exit out of said aperture, and without losing said mechanical properties;
    wherein the outside diameter of said flexible needle is less than 4 mm, and said non-axial aperture comprises a curved section of said cannula, exiting said cannula at essentially right angles to the axis of said cannula and having a radius of curvature sufficiently small that the exit aperture of said curved path is no more than the external diameter of said cannula, and
    wherein said mechanical properties are such that a 5 gm. force applied laterally to said flexible needle, would not cause a deflection of more than 1 mm at a point 30 mm. distant from a position at which said needle is clamped.

2. A robotic device according to claim 1 wherein coordinated control of the insertion motion of said cannula and said flexible needle and rotation of said rotatable element enables access to be obtained by said flexible needle to said target region of the brain.

3. A robotic device according to claim 1 wherein said flexible needle comprises a thin-wall tube having an oval or flattened oval cross sectional shape with its elongated dimension being perpendicular to the plane of bending of said flexible needle.

4. A robotic device according to claim 1 wherein said flexible needle comprises a thin-wall tube having an eye-shaped cross sectional shape with its elongated dimension being perpendicular to the plane of bending of said flexible needle.

5. A robotic device according to claim 1 wherein said flexible needle comprises a hollow chain of magnetized beads.

6. A robotic device according to claim 5 wherein said beads are magnetized in a direction such that they are attracted in a self-centering stack.

7. A robotic device according to claim 1 wherein said flexible needle comprises an annular inflated balloon.

8. A robotic device according to claim 1 wherein said flexible needle comprises an elongated tensegrity structure.

9. A robotic device according to claim 1, wherein said device is adapted to provide access to said target region of the brain with collateral trauma to non-accessed parts of the brain being approximately confined to a region having the width of said cannula.

10. A robotic device according to claim 1, wherein coordinated control of the insertion motion of said cannula and said flexible needle and rotation of said rotatable element enables access to be obtained by said flexible needle to said target region of the brain along an articulated path selected to avoid damage-prone regions of the brain.

11. A robotic device according to claim 1 wherein said flexible needle comprises a cutting tool, such that resection of a brain tumor can be performed with collateral trauma to those parts of the brain not being treated being approximately confined to a region having the width of said first cannulated needle.

12. A robotic device according to claim 1, wherein said flexible needle is adapted to be connected to an energy delivery system, such that ablation or optical or electro-treatment of a brain tumor can be performed with collateral trauma to those parts of the brain not being treated being approximately confined to a region having the width of said first cannulated needle.

13. A robotic device according to claim 12, wherein said flexible needle comprises an optical fiber for delivery of said energy.

14. A robotic device according to claim 1 wherein said flexible needle comprises a biopsy tool, such that biopsy samples may be obtained from regions of the brain at different positions laterally displaced from each other by distances substantially larger than the width of said first cannulated needle, with collateral trauma to those parts of the brain not being accessed being approximately confined to a region having the width of said first cannulated needle.

15. A robotic device according to claim 1, wherein said flexible needle comprises a drug delivery passage.

16. A robotic device according to claim 1, further comprising a set of preoperatively inserted markers for relating the position of said robotic device to the skull of a subject, such that the co-ordinate system of said robotic device can be registered to a preoperative image of the skull of said subject.

17. A robotic device according to claim 1, further comprising at least one position sensor disposed in the distal region of said flexible needle, such that the real time position of said flexible needle tip can be monitored intraoperatively, or in the distal region of said cannula, such that the real time position of the tip of said cannula can be monitored intraoperatively.

18. A robotic device according to claim 1, wherein said structure of said flexible needle is such that its flexibility is reduced on traversing said curved section of said cannula, and its mechanical properties are regained after deployment from said non-axial aperture.

19. A robotic device according to claim 1, wherein said flexible needle comprises a thin-wall tube having a cross sectional shape elongated in the direction perpendicular to the plane of bending of said needle, said shape having bistable conditions which switch on traversing said curved section of said cannula.

* * * * *